US00PP20458P2

(12) United States Plant Patent
Bailey

(10) Patent No.: US PP20,458 P2
(45) Date of Patent: Nov. 10, 2009

(54) ***SYRINGA* PLANT NAMED 'BAILNCE'**

(50) Latin Name: *Syringa reticulata*
Varietal Denomination: Bailnce

(75) Inventor: Rodney Bailey, Woodbury, MN (US)

(73) Assignee: Bailey Nurseries, Inc., St. Paul, MN (US)

( * ) Notice: Subject to any disclaimer, the term of this patent is extended or adjusted under 35 U.S.C. 154(b) by 74 days.

(21) Appl. No.: 12/148,304

(22) Filed: Apr. 18, 2008

(51) Int. Cl.
*A01H 5/00* (2006.01)

(52) U.S. Cl. ..... Plt./248

(58) Field of Classification Search ..... Plt./248
See application file for complete search history.

*Primary Examiner*—June Hwu
(74) *Attorney, Agent, or Firm*—Penny J. Aguirre

(57) ABSTRACT

A new cultivar of *Syringa reticulata,* 'Bailnce', characterized by its heavy and consistently annual blooming habit, its ability to produce blooms on young plants, its dark green leaves, its vase-shaped plant habit with horizontal branching, its essentially sterile flowers, its hardiness in U.S.D.A. Zones 3 to 7, and its trouble free culture with suitability for planting in residential, park, and commercial areas.

3 Drawing Sheets

Botanical classification: *Syringa reticulata.*
Variety denomination: 'Bailnce'.

BACKGROUND OF THE INVENTION

The present invention relates to a new and distinct cultivar of Japanese tree lilac, botanically known as *Lilac reticulata,* 'Bailnce' and will be referred to hereafter by its cultivar name, 'Bailnce'.

The inventor discovered 'Bailnce' as a naturally occurring whole plant mutation of *Syringa reticulata* in summer of 2000 in a residential cultivated area in Hastings, Minn. The parentage of 'Bailnce' is unknown.

Asexual reproduction of the new cultivar was first accomplished under the direction of the inventor by budding onto *Syringa reticulata* rootstock in August of 2000 in St. Paul, Minn. The characteristics of this cultivar have been determined to be stable and are reproduced true to type in successive generations.

SUMMARY OF THE INVENTION

The following traits have been repeatedly observed and represent the characteristics of the new cultivar as observed on the original tree for seven years and on propagated plants up to 7 years in age. These attributes in combination distinguish 'Bailnce' as a unique and cultivar of *Syringa reticulata.*

1. 'Bailnce' exhibits a heavy blooming habit, much greater than is typical for *Syringa reticulata.*
2. 'Bailnce' consistently produces flowers annually, whereas *Syringa reticulata* typically flowers biennually or bloom sparsely every other year.
3. 'Bailnce' begins to produce flowers at an earlier age than is typical of *Syringa reticulata;* 'Bailnce' produces flowers on plants one year in age.
4. 'Bailnce' has dark green leaves, slightly darker and larger than is typical of *Syringa reticulata.*

5. 'Bailnce' has a vase-shaped plant habit with dense horizontal branching, the habit of *Syringa reticulata* is most typically oval or rounded.
6. 'Bailnce' is essentially sterile as only a very few seedpods have been observed.
7. 'Bailnce' is suitable for planting in residential, park, and commercial areas for its blooming habit, plant habit, plant size, and trouble free culture.

'Bailnce' as a unique and unlike any existing cultivars of *Syringa reticulata* known to the inventor. 'Bailnce' can be compared to 'Ivory Silk' (not patented). 'Ivory Silk' is similar in having dark green foliage, a dense habit and better bloom than the species, however 'Ivory Silk' produces has less flowers, more seed capsules, a more oval to rounded habit, and foliage that is glabrous rather than puberulent.

BRIEF DESCRIPTION OF THE DRAWING

The accompanying colored photographs illustrate the overall appearance and distinct characteristics of the new *Syringa.* The photographs in FIG. 1, FIG. 3, and FIG. 4 were taken of the original mature tree in as discovered in Hastings, Minn. The photograph in FIG. 2 was taken in St. Paul, Minn. of a field planting of one year-old plants of 'Bailnce' as budded onto *Syringa reticulata* rootstock. The colors in the photographs are as close as possible with the digital photography techniques available, the color values cited in the detailed botanical description accurately describe the colors of the new *Syringa.*

DETAILED BOTANICAL DESCRIPTION

Figure 1:
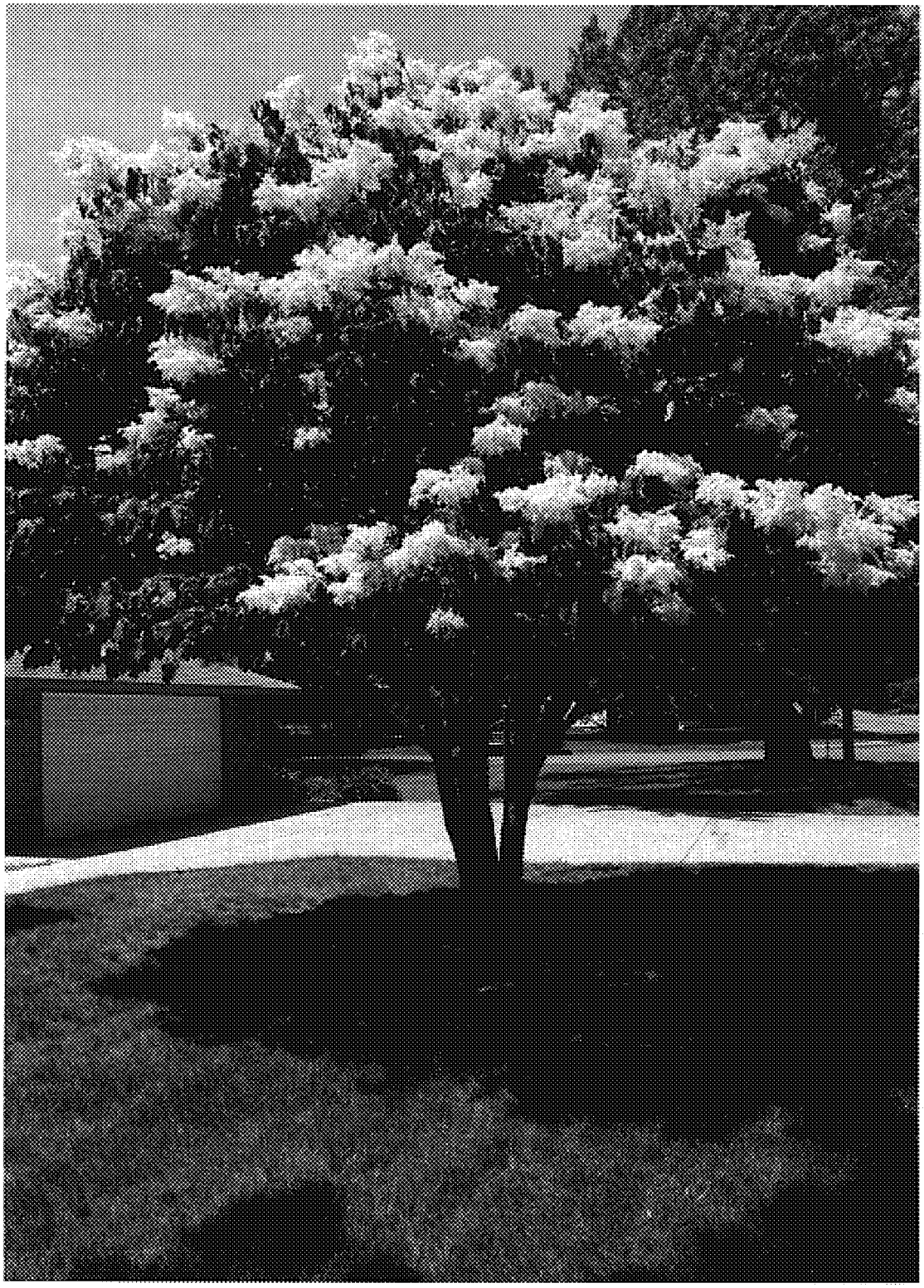
FIG. 1 illustrates the plant habit and of quantity of bloom observed on 'Bailnce'.
Figure 2:
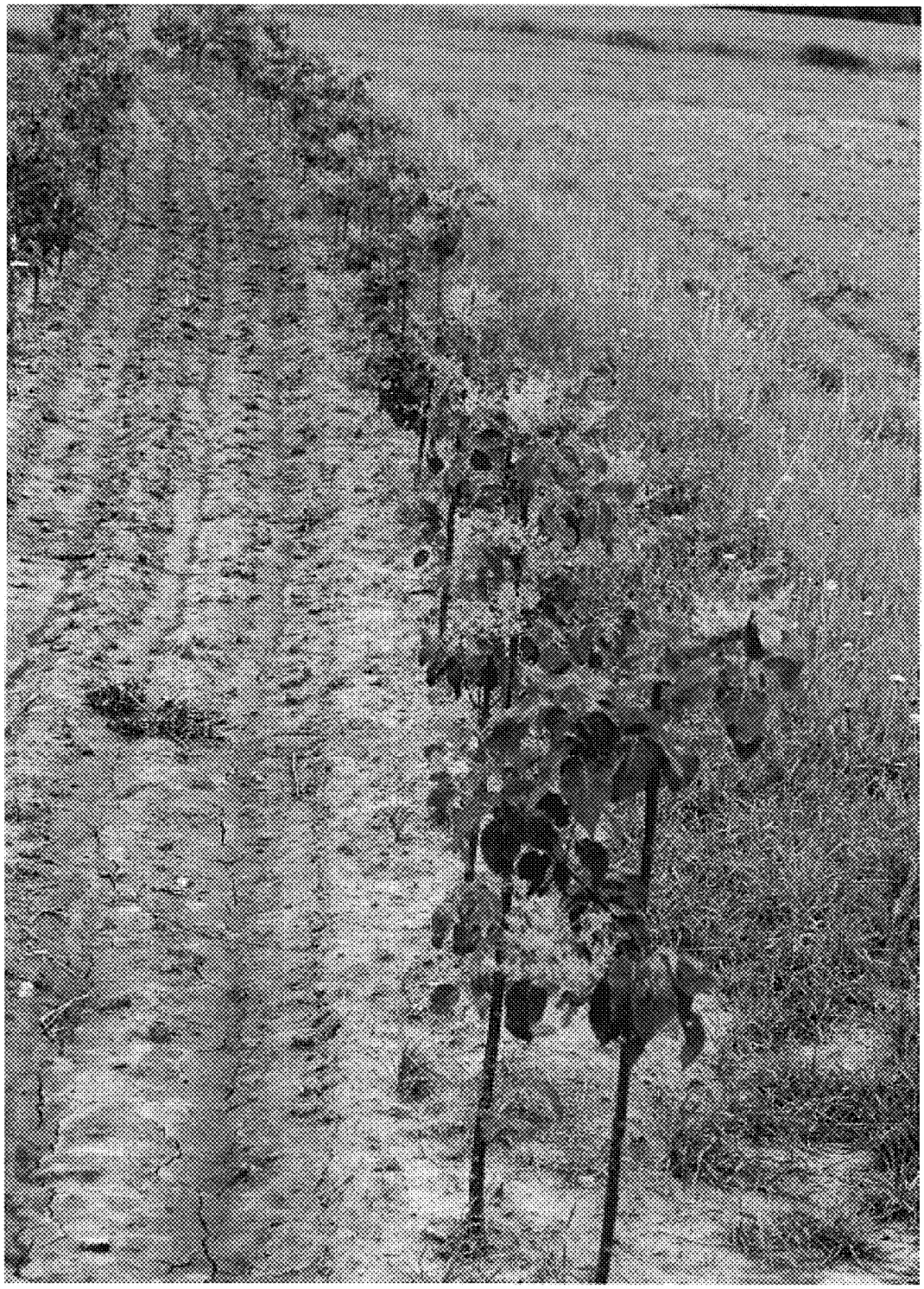
FIG. 2 illustrates the characteristics of 'Bailnce' to produce blooms on young plants.
Figure 3:
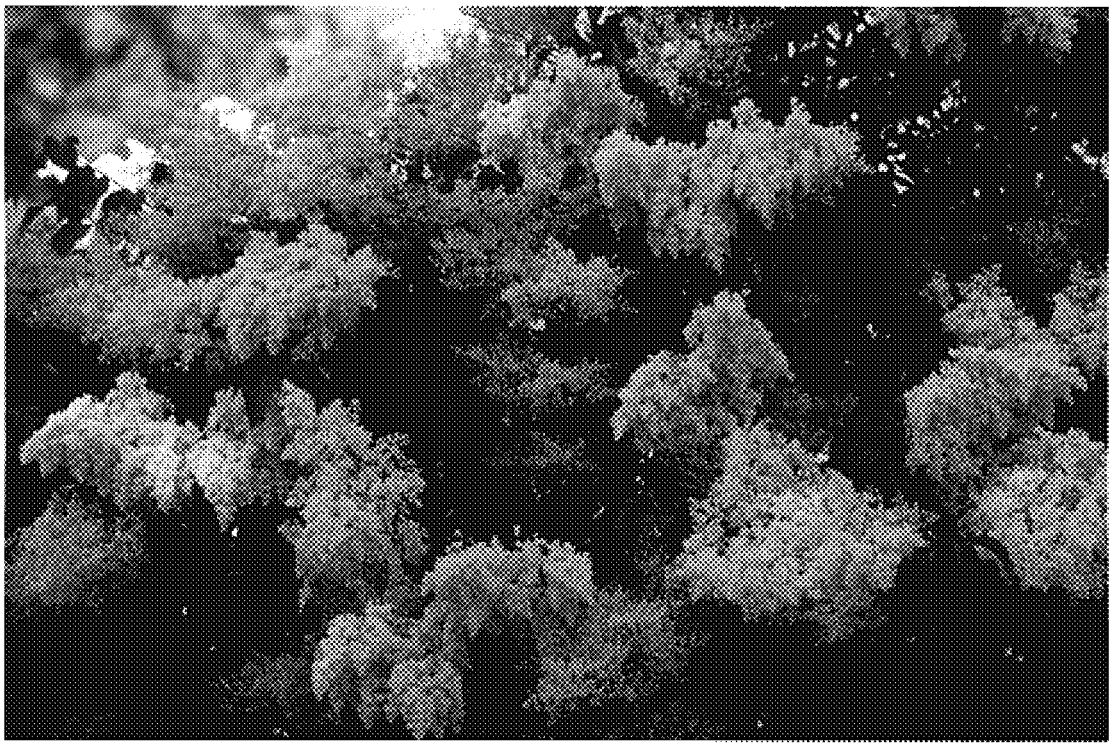
FIG. 3 provides a view of inflorescences of 'Bailnce' in various stages of development.
Figure 4:
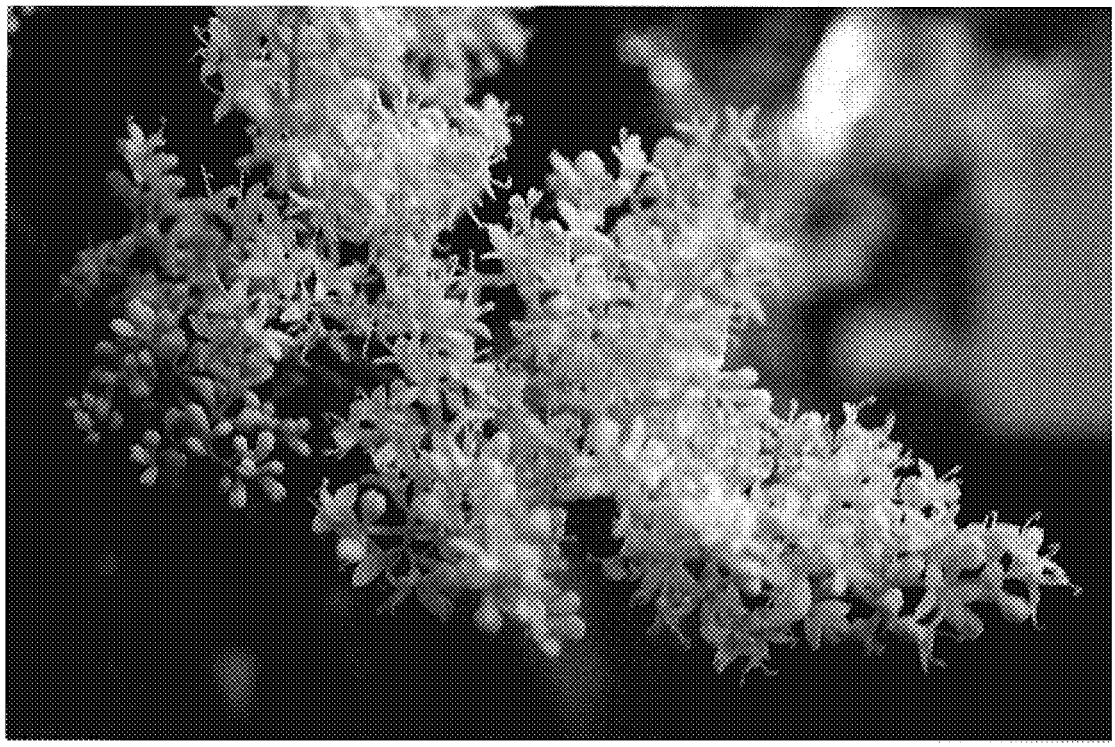
FIG. 4 provides a close-up view of an inflorescence of 'Bailnce'.

The following is a description of the new cultivar as observed for 7 years on the original tree with the detailed botanical data taken from a 3 year-old plant that was budded onto *Syringa reticulata* rootstock and finished in a 3-gallon container. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—Two to three weeks in early summer on previous season's wood; blooming period is temperature dependent with shorter bloom period with warm temperatures.

*Plant habit.*—Vase-shaped with dense horizontal branching.

*Height and spread.*—Mature trees reaches about 6.1 m (20 ft) in height and about 5.5 m (18 ft) in width.

*Hardiness.*—U.S.D.A. Zone 3 to 7.

*Diseases and pests.*—No susceptibility or resistance to diseases or pests has been observed. *Syringa reticulata* is generally pest and disease free and tolerant to urban pollution.

*Root description.*—Fibrous.

Growth and propagation:

*Propagation.*—Budding onto *Syringa reticulata* rootstock.

*Growth rate.*—Vigorous.

Bark description:

*Surface texture.*—Relatively smooth.

*Bark color.*—201A and 200A.

*Lenticels.*—About 1 mm in height and 3 mm in length, 7 lenticels per cm square, and 201D in color.

Stem description:

*Shape.*—Nearly quadrangular.

*Stem color.*—Young shoots 144A with sparse lenticels 158B, previous seasons twigs 197C, mature wood N199B with overlay of 197C and lenticels 158B.

*Stem size* (*3 year-old tree*).—Main stem up to 6 cm in width and 1.8 m in height, lateral branches average 1 cm in width, new growth is an average of 5 mm in width.

*Stem surface.*—Glabrous with lenticels.

*Internode length.*—Average of 6 cm between lateral branches and average of 4 cm on new growth.

*Branching.*—Dense, horizontal.

Foliage description:

*Leaf shape.*—Ovate.

*Leaf division.*—Simple.

*Leaf base.*—Rounded (attenuate when young).

*Leaf apex.*—Acuminate with undulating apex.

*Leaf fragrance.*—None.

*Leaflet venation.*—Pinnate, only midrib is conspicuous, N144A in color On upper surface and 146D in color on lower surface.

*Leaflet margins.*—Entire with slight undulations.

*Leaf arrangement.*—Opposite.

*Leaf attachment.*—Petiolate.

*Leaf surface.*—Dull and puberulent on upper surface and lower surface.

*Leaf size.*—Average 16.5 cm in length and 10 cm in width of mature leaf.

*Leaf quantity.*—About 40 on a branch 60 cm in length.

*Leaf color.*—Young leaves; 137A on upper surface and color between 138A and 138B on lower surface, mature; 147A on upper surface and 138A with pubescence of 138B on lower surface.

*Petioles.*—Average of 2.2 cm in length, 2.7 mm in width, color 144A to 144B.

*Stipules.*—Absent.

Inflorescence description:

*Inflorescence type.*—Thyrse compound panicles on terminals and laterals of previous years growth, ovate in overall shape.

*Inflorescence size.*—Reach up to 27 cm in length and width with branches about 13 cm in length and 7 cm in width.

*Rachis.*—Nearly quadrangular in shape, up to 27 cm in length and 4 mm in width with secondary branches an average of 13 cm in length and 2 mm in width, 144A in color with lenticels 158B, surface is glabrous, average internode length for secondary branches 2 cm, tertiary branches average 2 cm in length and 1 mm in width with an internode length of about 1 cm and are 11C in color.

*Pedicels.*—About 3 mm in length and 1 mm in width, 11C in color, glabrous surface, typically 3 flowers per pedicel.

*Flower buds.*—Obovate in shape, 4 mm in depth and 2 mm diameter, 155B in color with sepal portion 150D.

*Flower fragrance.*—Strong lilac scent.

*Persistence of flowers.*—Self-cleaning, calyx persistent.

*Lastingness of flowers.*—Individual panicles bloom for about 2 weeks, depending on temperature.

*Flower quantity.*—Numerous, about 1,000 to 2,000 per compound panicle.

*Flower type.*—Star-shaped with spreading petals.

*Flower aspect.*—Outward from pedicel in threes.

*Flower size.*—About 7 mm in diameter and 4 mm in depth.

*Petals.*—4, about 4 mm in length and 1.2 mm in width, fused only at base, elliptic in shape, truncate base, acute apex, 155C in color.

*Calyx.*—Campanulate, about 2 mm in depth and 1 mm in width, comprised of 4 fused sepals with tips unfused with acute apices, glabrous surface, 150D in color.

Reproductive organs:

*Pistils.*—1, inserted deep into calyx, filaments; minute if present, stigma; too minute to measure, appears plumose and about 150D in color; superior; very small, 2-carpelled.

*Stamens.*—2, exerted beyond corolla, filaments; 3 mm in length, 155C in color, anthers; 1 mm in length, about 150D in color, pollen; abundant and 150C in color.

*Fruit and seed.*—Essentially sterile, seed capsules have been observed on rare occasion but were not produced on plants available for data collection.

It is claimed:

1. A new and distinct cultivar of *Lilac* plant named 'Bailnce' as herein illustrated and described.

* * * * *